United States Patent [19]

Hirofuji

[11] Patent Number: 5,752,975
[45] Date of Patent: May 19, 1998

[54] DEVICE FOR INCREASING THE ELECTRIC FIELD OF THERAPEUTIC APPARATUSES

[75] Inventor: Michio Hirofuji, Tokyo, Japan

[73] Assignee: Mesotes Co., Ltd., Tokyo, Japan

[21] Appl. No.: 749,547

[22] Filed: Nov. 15, 1996

[30] Foreign Application Priority Data

Nov. 15, 1995 [JP] Japan .................... 7-321031

[51] Int. Cl.⁶ .................................................. A61N 1/40
[52] U.S. Cl. ........................................................ 607/2
[58] Field of Search ........................ 607/2, 154–156, 607/101–103; 606/41–42

[56] References Cited

U.S. PATENT DOCUMENTS 2,220,269  11/1940  Patzold ........................... 607/154
2,223,447  12/1940  Hathaway ........................ 607/154
3,077,195   2/1963  Folsche .......................... 607/156

FOREIGN PATENT DOCUMENTS 524879   8/1977  Japan .
1033143  8/1983  U.S.S.R. .......................... 607/154
2135891  9/1984  United Kingdom .............. 607/154

*Primary Examiner*—William E. Kamm

[57] ABSTRACT

A small device for increasing the electric field of a therapeutic apparatus utilizing electric potential. The device may be inexpensively produced, exhibits high and stable topical therapeutic effects, and is easy to handle. The device for increasing electric field includes a grounded conductor and an insulating case covering the conductor such that the distance between the outer surface of the conductor and the outer surface of the insulating case is fixed when the device is used.

20 Claims, 10 Drawing Sheets

DEVICE FOR INCREASING THE ELECTRIC FIELD OF THERAPEUTIC APPARATUSES

BACKGROUND OF THE INVENTION

I. Field of the Invention

The present invention relates to a device for increasing electric field of therapeutic apparatuses utilizing electric potential, which are used for treating skin conditions, poor circulation and other diseases.

II. Description of the Related Art

In therapies utilizing electric field, what plays a basic role is not the electric potential per se applied to a patient, but the intensity of electric field.

Thus, in order to increase the electric field applied to the portion to be treated, the present inventor previously developed a device for increasing electric field of therapeutic apparatuses utilizing electric potential for applying an electric field to a portion to be treated by directly contacting a therapeutic plate with the insulated human body so as to apply a high voltage from a generator of electric field. This device included a grounded conductor and an insulating case covering the conductor as disclosed in Japanese Patent Publication (Kokoku) No. 52-4879.

This device for increasing electric field is used by laying the device on a bed and laying the patient on the device. An output terminal of the electric field generator is connected to a therapeutic plate and a grounded terminal is connected to a conductor of the device for increasing electric field. The therapeutic plate is made to directly contact the patient. The electric field applied to the patient is generated between the therapeutic plate and the conductor of the device for increasing the electric field. With this apparatus, the electric field applied to the patient is high and does not fluctuate, so that the therapeutic effect is advantageously constant.

However, this device for increasing electric field is overlaid on a bed and the patient is laid on the device, so that the device is large and expensive. Thus, in the above-mentioned patent publication, a compact device for increasing electric field comprising a conductor which is directly enclosed in a sponge is proposed.

However, the device for increasing electric field comprising a conductor which is directly enclosed in a sponge is not practical because the sponge lacks durability. Further, the thickness of the sponge unintentionally varies because of the fluctuation of the thickness of the sponge, or due to the fluctuation of the force applied to the sponge when the conductor is enclosed in the sponge. Still further, due to the static electricity caused by internal friction in the sponge, the conductor is not completely grounded. Therefore, the intensity of the electric field applied to the patient is not constant, so that stable therapeutic effect cannot be obtained.

SUMMARY OF THE INVENTION

Accordingly, an object of the present invention is to provide a compact device for increasing electric field of therapeutic apparatuses utilizing electric potential which may be produced inexpensively, exhibits high and stable topical therapeutic effects, and is easy to handle.

To attain this object, the present inventor intensively studied theoretically and experimentally to discover that a material such as sponge which contains air, in which internal friction is likely to occur, and which is elastic and deformable, is not preferred as the insulator for enclosing the conductor. Instead materials having a certain rigidity, and by which a constant distance is surely formed between the conductor and the skin of patient when the device is mounted on a human body are preferred in promoting the therapeutic effects.

Accordingly, the present invention provides a device for increasing electric field of therapeutic apparatuses utilizing electric potential for applying an electric field to a portion to be treated of a human body by directly contacting a therapeutic plate with an insulated human body so as to apply a high voltage from a generator of electric field the device includes a grounded conductor and an insulating case covering said conductor such that the distance between the outer surface of said conductor and the outer surface of said insulating case is fixed when the device is used.

According to the present invention, the device for increasing electric field can be made small. Therefore, electric field can be concentrated to the affected portion to be treated and to the vicinity thereof, so that excellent topical therapeutic effects can be obtained for relieving such conditions as a stiff shoulder, and poor skin circulation. Further, the device can be produced inexpensively. Still further, unlike the large device which is used by being overlaid on a bed, the device according to the present invention can be used when the patient is sitting on a chair, so that the therapy does not require large space, and the device is easy to handle.

Moreover, since the distance between the outer surface of the conductor and the outer surface of the insulating case is fixed when the device is used, stable electric field can be applied consistently. For example, in cases where the distances in the direction of thickness between the outer surfaces of the conductor and the outer surfaces of the insulating case are about 5 cm, respectively, earth potential always exists at a distance of 5 cm from the skin, so that stable and strong electric field (negative charge e$^-$) can be focused to the affected portion requiring strong electric field.

Still further, since an insulating case (especially a plastic case) is used, the device is light in weight, inexpensive and relatively rigid, so that unlike sponge, it is not likely to be damaged and earth potential is surely attained.

DETAILED DESCRIPTION OF THE PREFERRED EMBODIMENTS

The grounded conductor of the device for increasing electric field may preferably be a plate made of a conductive material such as copper, iron or the like, which is unremovably incorporated into an insulating case. As this conductor plate, one which is the same as or similar to the therapeutic plate that is to be contacted with a portion of the human body may be employed. Alternatively, the grounded conductor may be a conductor plate removably inserted into the insulating case. In this case, it is preferred to provide an insulating coating on the conductor plate.

The insulating case of the device for increasing electric field may be a plastic case or the like in which the grounded conductor may be fitted. The case may be either hollow or solid. The distances (indicated by "L" in FIGS. 3, 5 and 7, hereinbelow described in more detail) in the direction of the thickness of the insulating case between the outer surfaces of the conductor plate and the outer surfaces of the insulating case, respectively, are preferably 4 cm to 8 cm, more preferably 5 cm to 6 cm. In cases where negative charge of a direct voltage of 200V to 400V is applied to the human body through the therapeutic plate, the distances are usually and preferably about 5 cm. In this case, when the device for increasing electric field is contacted with the human body, there is a distance of about 5 cm between the skin of the human body and the grounded conductor. By virtue of this distance, the electric field which is the most effective is generated at the portion contacted with the device and in the vicinity thereof, so that high therapeutic effects are obtained stably. If the distance is about 5 cm, the negative charge to be applied may be adjusted depending on the sex and age of the patient, and on the purpose of therapy so as to attain more effective therapy.

Specific preferred embodiments of the present invention will now be described referring to the accompanying drawings.

Figure 1:
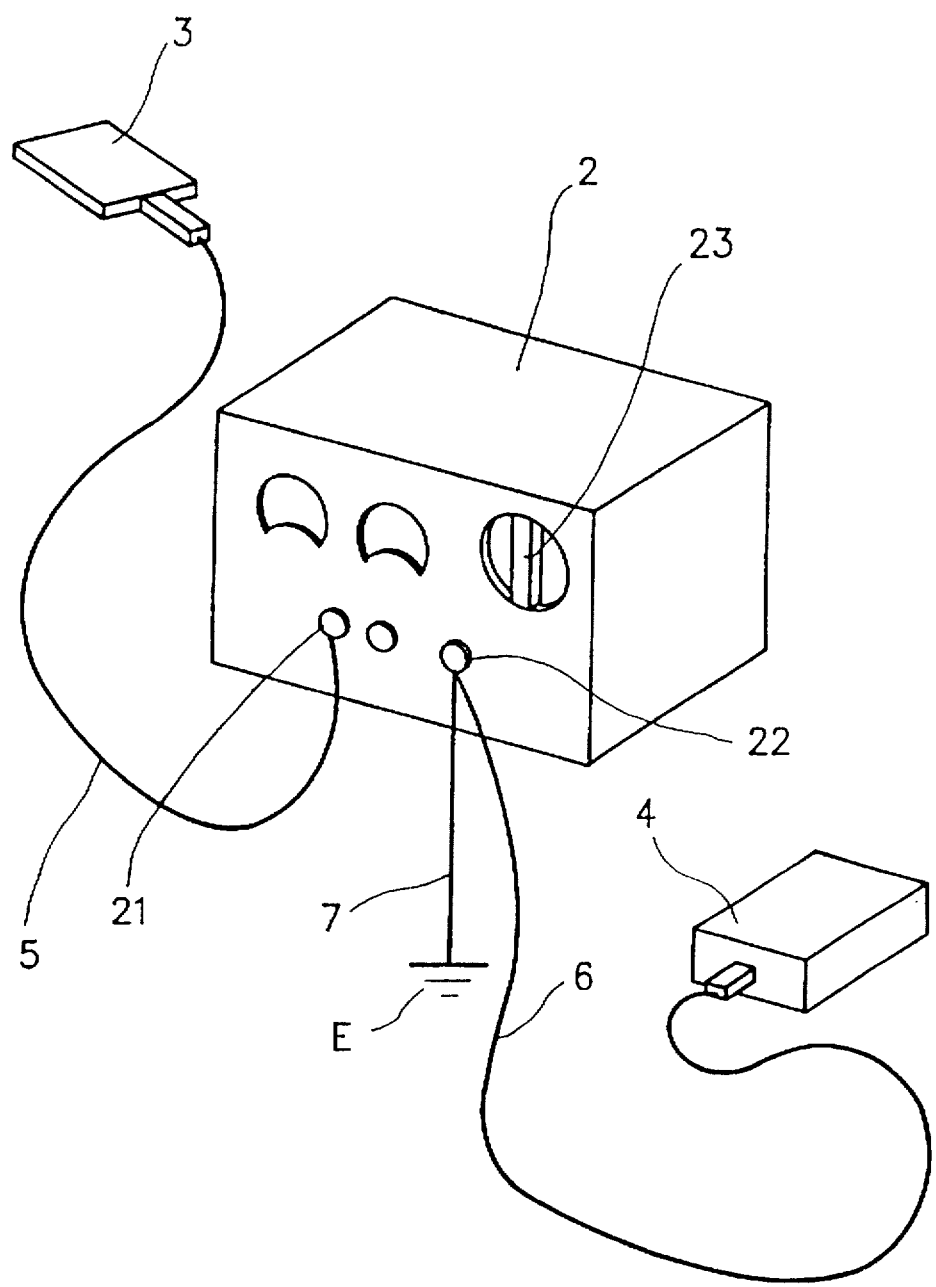
FIG. 1 is a perspective view showing the entire therapeutic apparatus utilizing electric potential.

Referring to FIG. 1, a therapeutic apparatus 1 utilizing electric potential comprises an electric field generator 2, a therapeutic plate for applying negative electric potential from the generator 2 to a patient, and a device 4 for increasing the intensity of the electric field at the portion to be treated.

The generator 2 comprises an output terminal 21, an earth terminal 22 and a timer 23, as well as a rectifier and a capacitor therein. The generator 2 raises the supplied alternating voltage to 250V to 300V and simultaneously rectifies (converts the alternating voltage to direct voltage) the voltage so as to charge the capacitor. The negative side (the side in which the negative charge e⁻ is accumulated) of the capacitor is connected to the output terminal 21 and the positive side of the capacitor is connected to the earth terminal 22. The therapeutic plate 3 is connected to the output terminal 21 through a lead wire 5. The device 4 for increasing electric field is connected to the earth terminal 22 through a lead wire 6. The earth terminal 22 is grounded through a lead wire 7.

The voltage generated by the generator 2 is usually about 250V to 300V. However, a voltage between 200V and 400V may be selected depending on the purpose of therapy. The waveform of the voltage may be negative direct voltage, negative pulsating voltage or the like, and may be selected depending on the purpose of therapy.

The therapeutic plate 3 is made to directly contact a portion of an insulated patient M (see FIG. 10) and negative electric potential is directly applied to the human body through the therapeutic plate 3. Simultaneously, the device 4 for increasing the electric field is made to contact an affected portion to be treated of the patient. By so doing, a capacitor is formed between the human body and the device 4 (earthed potential), so that electric field (negative charge e⁻) is concentrated to the affected portion of the patient and the vicinity thereof of the insulated human body. By virtue of the concentration of the negative charge e⁻, concentration, temperature and pressure of the human body are raised, so that cells having decreased functions may be stimulated so as to acquire the normal functions. As a result, improvement of skin, relief of stiff shoulder and the like may be attained.

Figure 2:
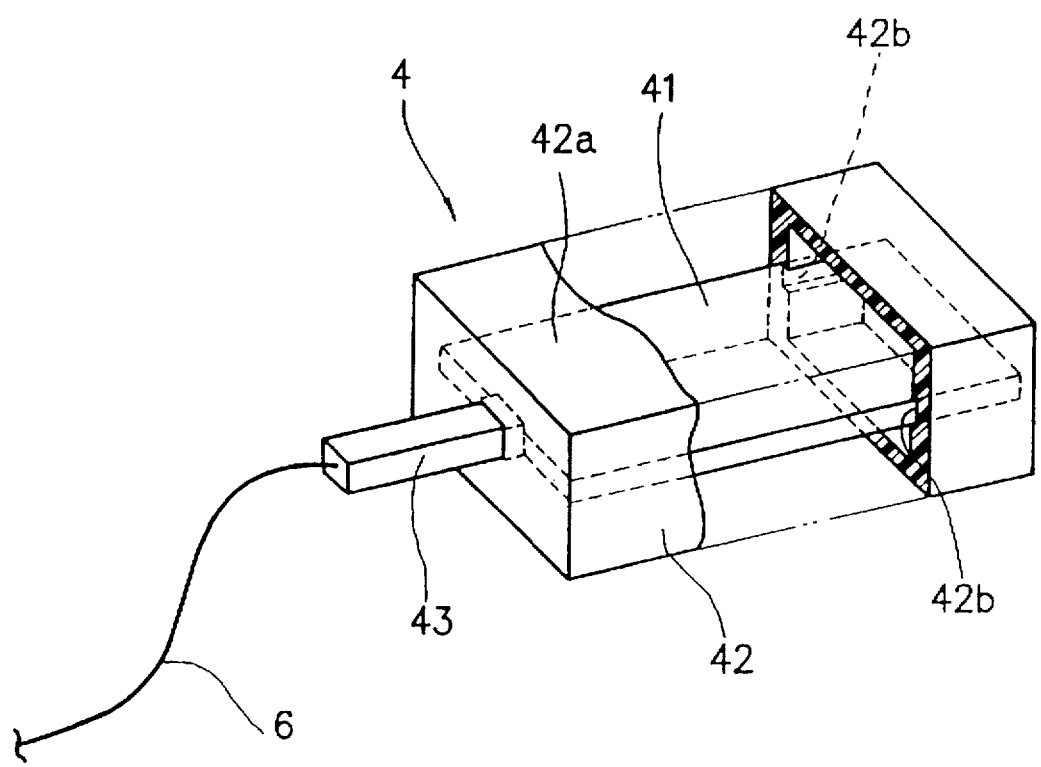
FIG. 2 is a perspective and partially sectional view showing a first embodiment of the device for increasing electric field according to the present invention.
Figure 3:
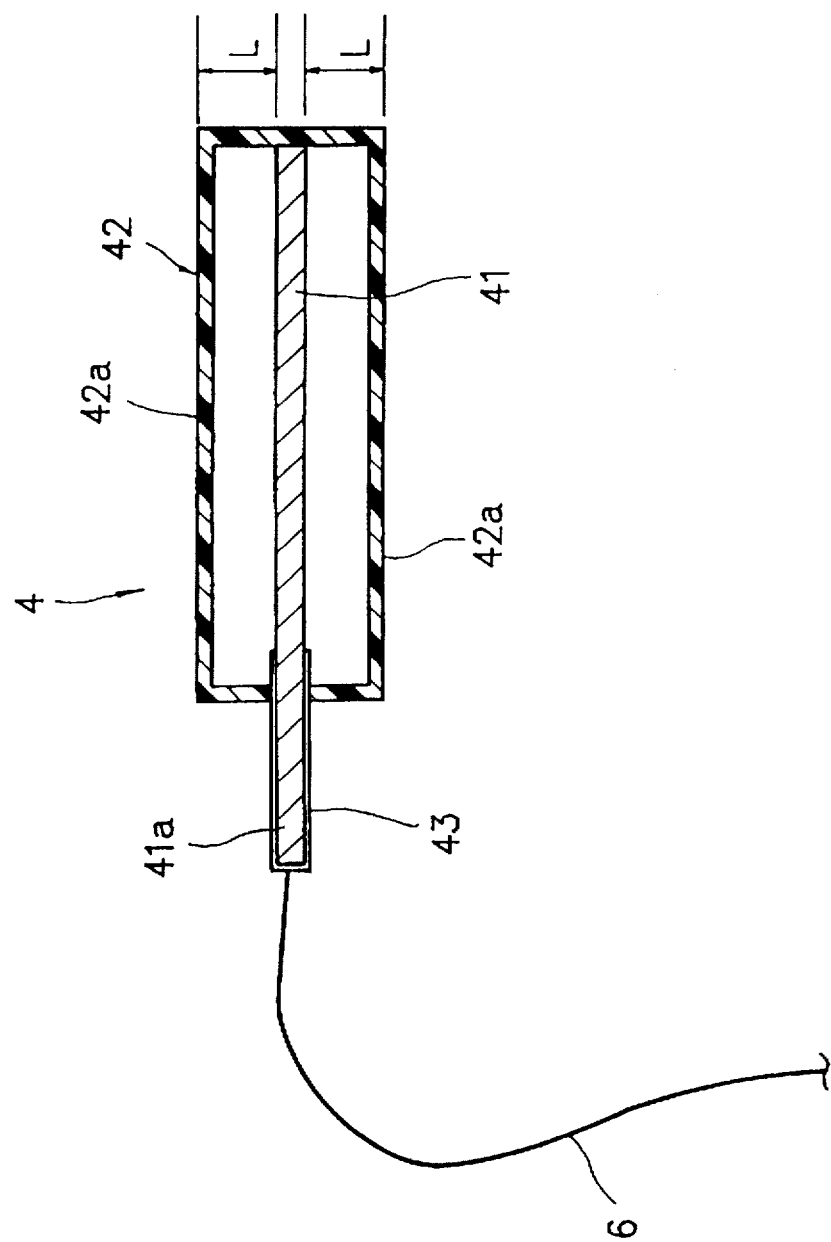
FIG. 3 is a sectional side view showing the first embodiment of the device for increasing electric field according to the present invention.

FIGS. 2 and 3 show a first embodiment of the device for increasing electric field according to the present invention. In this embodiment, a conductor plate is unremovably incorporated into a hollow insulating case. By using a hollow insulating case, the device has a light weight.

The device 4 for increasing electric field comprises a conductor plate 41 grounded through a lead wire 6 and a rectangular parallelepiped hollow insulating case 42 made of a plastic or the like which unremovably incorporates the conductor plate 41. There are distances L, L of about 5 cm in the direction of thickness of the insulating case 42 between the surfaces of the conductor plate 41 and the surfaces 42a, 42a of the insulating case 42, respectively, at least one of the surfaces 42a, 42a being contacted with the affected portion of the human body. The distances L, L may be appropriately selected depending on the voltage applied. Usually, in cases where a direct voltage of about 250V to 300V is applied, the distances may be about 5 cm as mentioned above. A connection terminal portion 41a of the conductor plate 41 is coated with an insulating coating layer 43.

The conductor plate 41 may be one similar to the above-mentioned therapeutic plate 41. Needless to say, a conductor plate which is the same as the therapeutic plate 3 may be incorporated into the insulating case to form the device for increasing electric field. In this case, it is not necessary to produce a type of conductor plate which is different from the therapeutic plate. It is preferred to cover the exposed portion of the conductor plate with an insulating coating 43.

The device 4 for increasing electric field may be produced by inserting the grounded conductor plate 41 into mounting grooves 42b, 42b formed in both sides of the central portion of the hollow insulating case 42 made of plastic so as to position the conductor plate 41, and integrally incorporating the conductor plate 41 in the insulating case 42. In this case, halves of the hollow insulating case 42 may first be provided, and after incorporating the conductor plate therein, the halves of the hollow insulating case 42 may be fitted.

Figure 4:
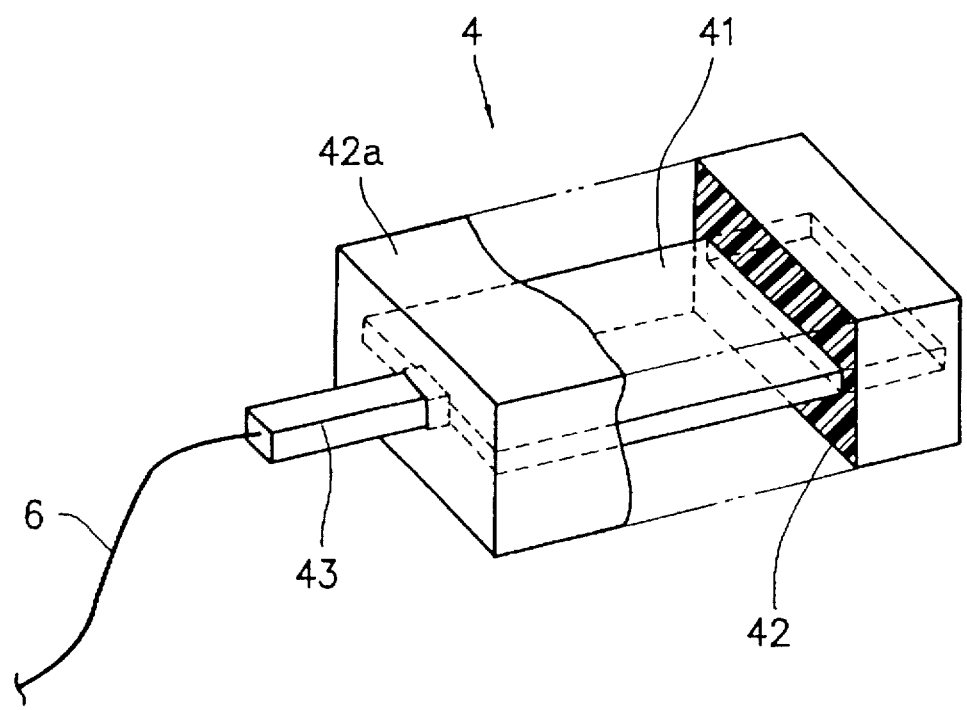
FIG. 4 is a perspective and partially sectional view showing a second embodiment of the device for increasing electric field according to the present invention.
Figure 5:
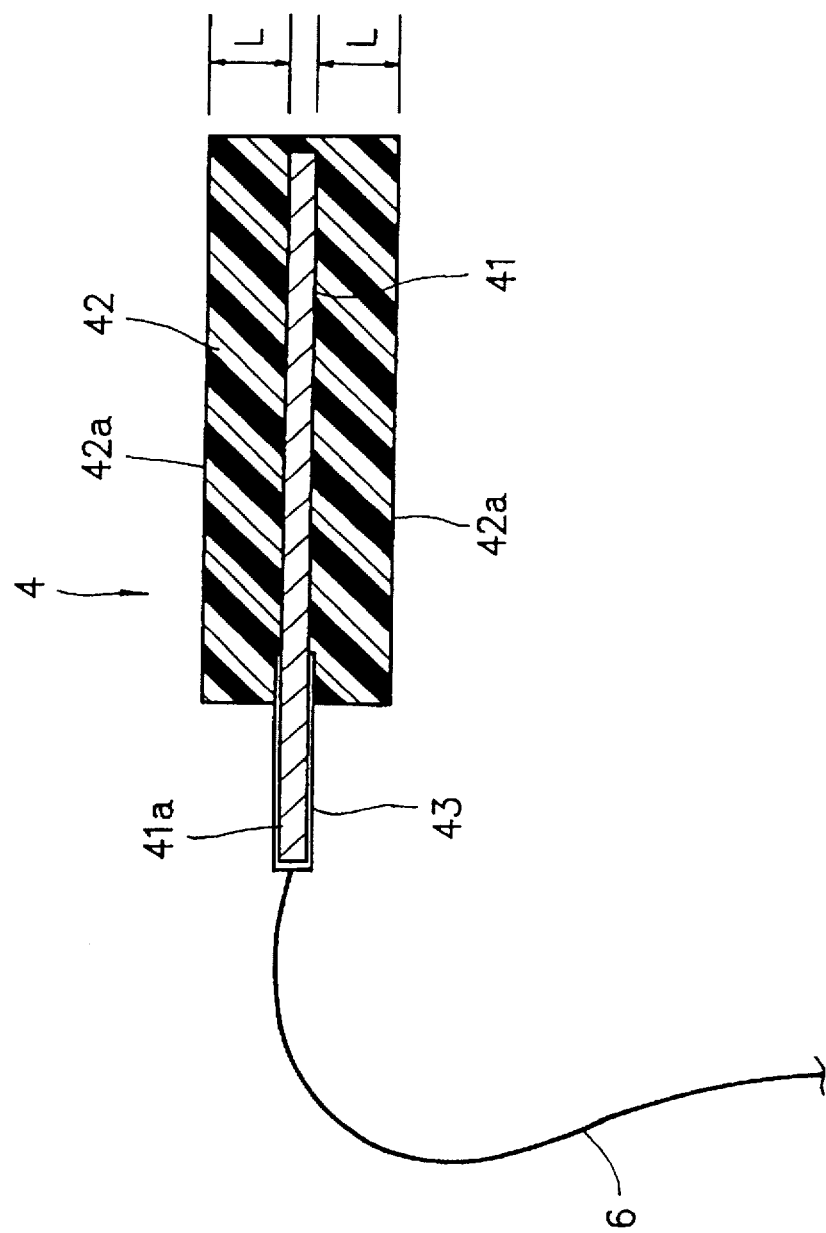
FIG. 5 is a sectional side view showing the second embodiment of the device for increasing electric field according to the present invention.

FIGS. 4 and 5 show a second embodiment of the device for increasing electric field. In this embodiment, a conductor plate is unremovably incorporated into a solid insulating case, so that the device is slightly heavy. The difference between the first and second embodiments is that a solid insulating case is used in the second embodiment in place of the hollow insulating case used in the first embodiment, and all other features of these embodiments are the same.

That is, the device 4 for increasing electric field comprises a conductor plate 41 grounded through a lead wire 6 and a rectangular parallelepiped solid insulating case 42 made of a plastic or the like which unremovably incorporates the conductor plate 41. There are distances L, L of about 5 cm in the direction of thickness of the insulating case 42 between the surfaces of the conductor plate 41 and the surfaces 42a, 42a of the insulating case 42, respectively, at least one of the surfaces 42a, 42a being contacted with the affected portion of the human body. The distances L, L may be appropriately selected depending on the voltage applied. A connection terminal portion 41a of the conductor plate 41 is coated with an insulating coating layer 43. As in the first embodiment, the conductor plate 41 may be one which is the same as the therapeutic plate 3.

Figure 6:
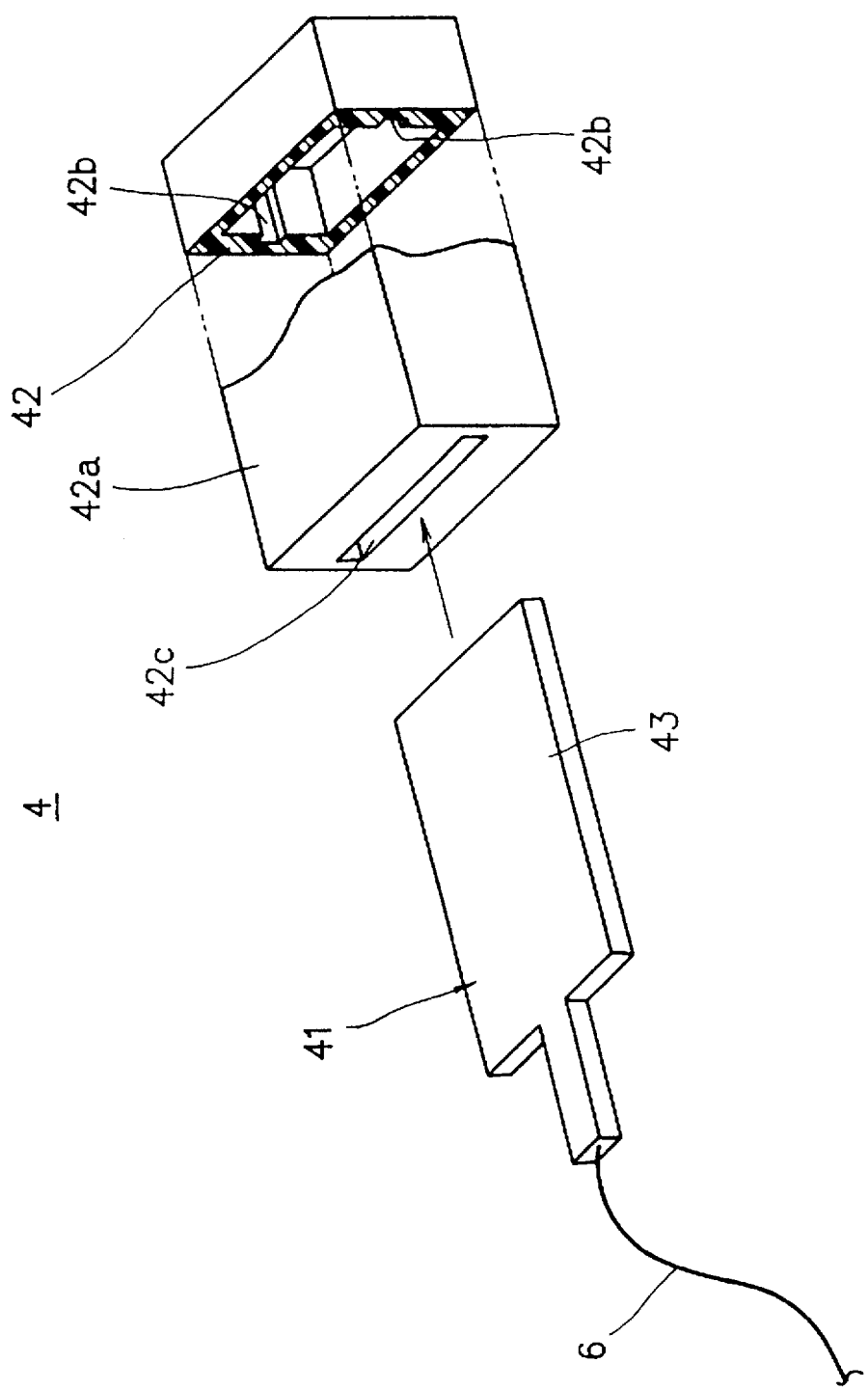
FIG. 6 is a perspective and partially sectional exploded view showing a third embodiment of the device for increasing electric field according to the present invention.
Figure 7:
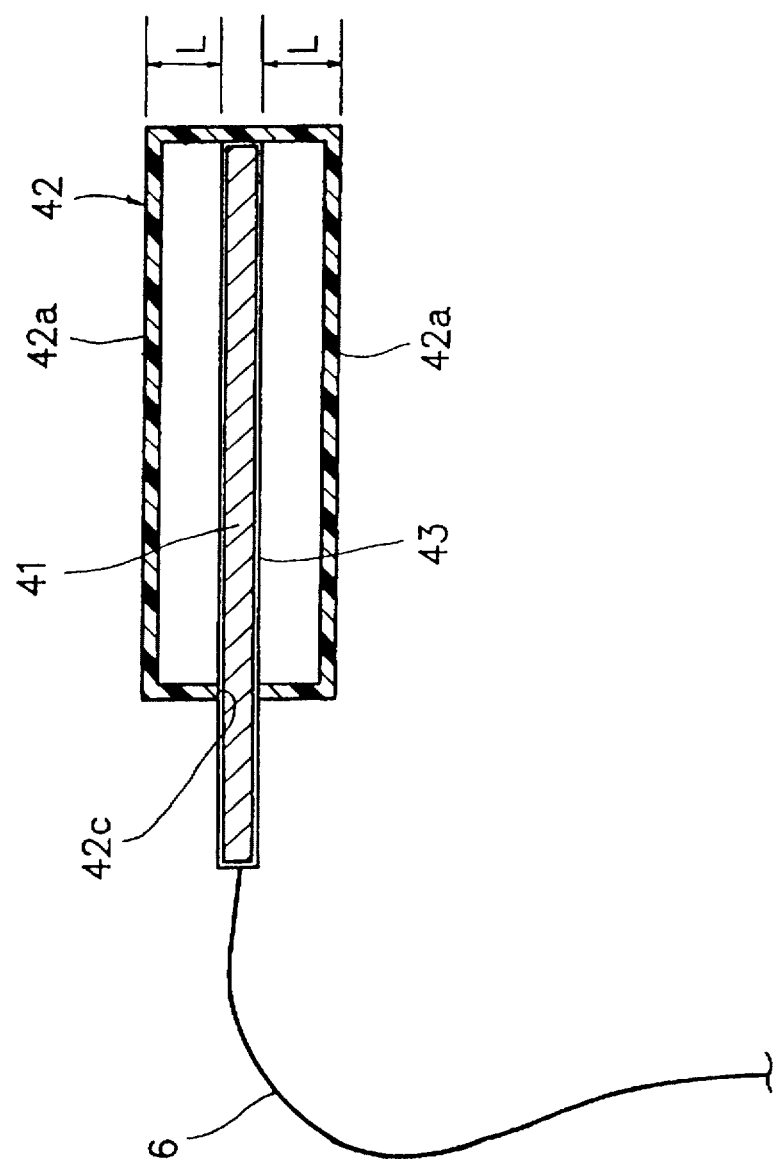
FIG. 7 is a sectional side view showing the third embodiment of the device for increasing electric field according to the present invention.
Figure 8:
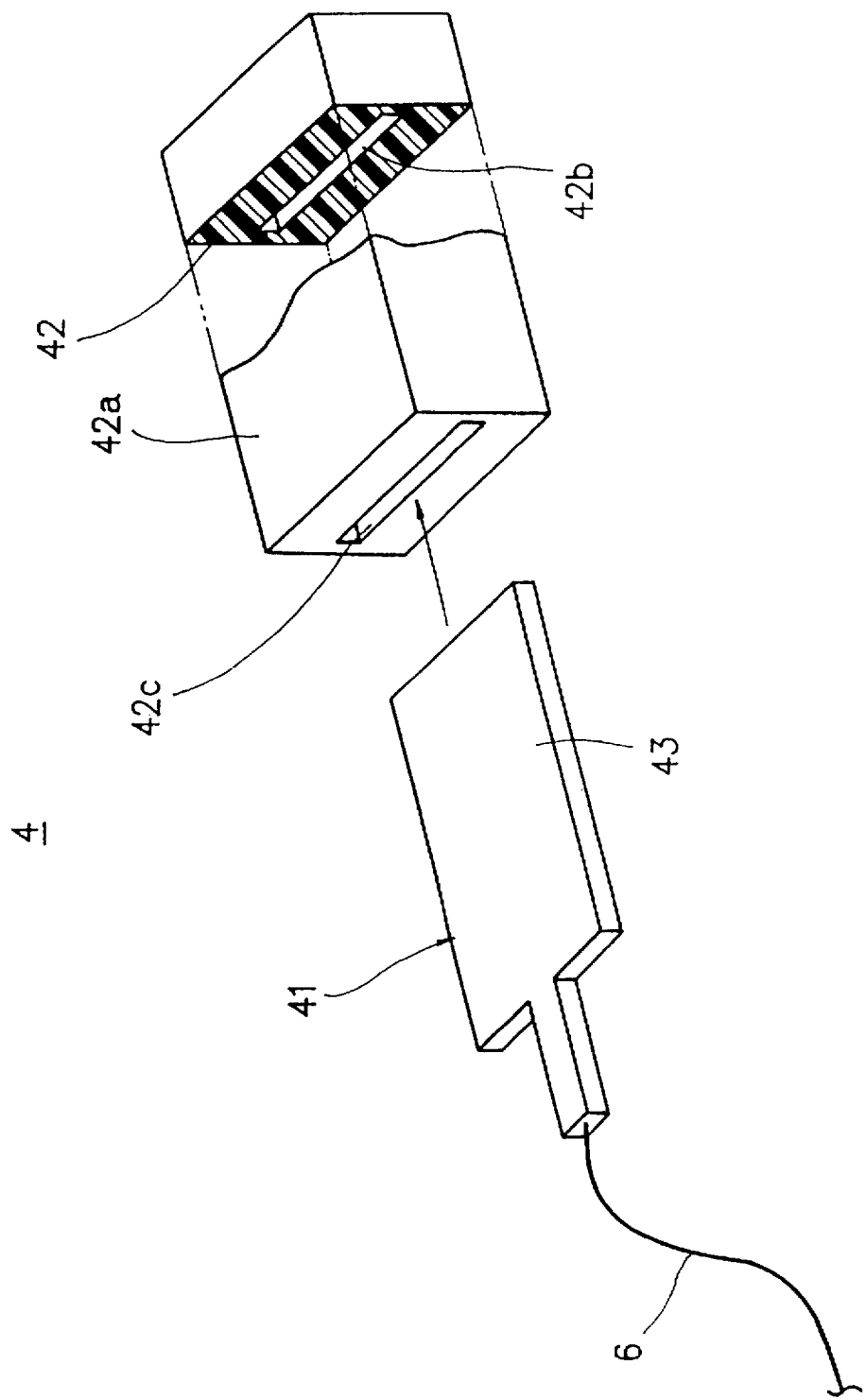
FIG. 8 is a perspective and partially sectional view showing a fourth embodiment of the device for increasing electric field according to the present invention.
Figure 9:
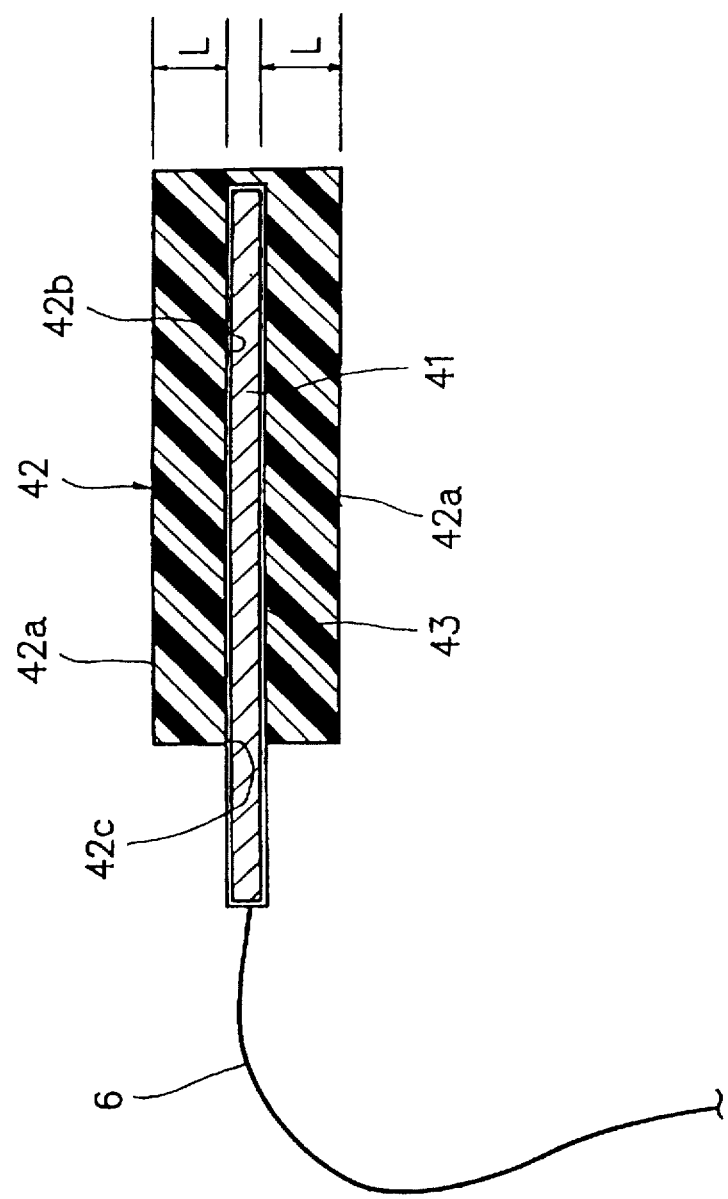
FIG. 9 is a sectional side view showing the fourth embodiment of the device for increasing electric field according to the present invention.

FIGS. 6 and 7 show a third embodiment of the device for electric field according to the present invention. In this embodiment, a conductor plate which has an insulating coating on the entire surface thereof is inserted into a hollow insulating case, and the conductor plate having the insulating coating can be easily removed.

In this embodiment, the device 4 for increasing electric field comprises a conductor plate 41 grounded through a lead wire 6 and a rectangular parallelepiped hollow insulating case 42 made of a plastic or the like. The conductor plate 41 is grounded through a lead wire 6 and inserted into the insulating case 42. There are distances L, L of about 5 cm in the direction of thickness of the insulating case 42 between the surfaces of the conductor plate 41 and the surfaces 42a, 42a of the insulating case 42, respectively, at least one of the surfaces 42a, 42a being contacted with the affected portion of the human body. The distances L, L may be appropriately selected depending on the voltage applied. Usually, in cases where a direct voltage of about 250V to 300V is applied, the distances may be about 5 cm as mentioned above.

The conductor plate 41 may be one similar to the above-mentioned therapeutic plate 41. Needless to say, a conductor plate which is the same as the therapeutic plate 3 may be grounded. In this case, the plate which is the same as the therapeutic plate 3 is coated with the insulating coating and the resultant is inserted into the insulating case 42, thereby forming the device 4 for increasing electric field.

The device 4 for increasing electric field may be assembled by inserting the grounded conductor plate 41 into a mounting groove 42b formed in the central portion of the plastic insulating case 42 through a slot 42c formed in the end face of the insulating case, which slot 42c is connected to the groove 42b.

In the first to fourth embodiments mentioned above, between the conductor plate 41 and the surface 42a of the insulating case 42, hollow space is formed (first and third embodiments) or the space is not hollow but solid (second and fourth embodiments). Any modifications thereof in which the conductor plate 41 is arranged in the insulating case 42 and the distances L, L are formed between the surfaces 42a, 42a to be contacted with human body and the surfaces of the conductor plate 41 are included in the scope of the present invention.

Further, in these embodiments, the distances L, L are about 5 cm, respectively. However, the position of the mounting groove 42b in which the conductor plate 41 is inserted may be changed. For example, the distances may be 4 cm and 6 cm, respectively. In this case, the surface to be contacted with the patient may be selected so that the desired intensity of electric field may be applied to the patient depending on the conditions of the patient and purpose of therapy.

In cases where the conductor plate is inserted into the insulating case as in the third and fourth embodiments, a plurality of steps of mounting grooves 42b may be formed in the insulating case 42. In this case, a plurality of positions for mounting the conductor plate are available, so that the mounting position of the conductor plate 41 having the insulating coating may be changed depending on the conditions of the patient and purpose of therapy.

By forming the device 4 for increasing electric field as described above, a distance L, e.g., about 5 cm, is formed between the skin of the patient and the grounded conductor plate 41 located at the central portion of the insulating case 42. By virtue of this fixed distance L, a constant effective intensity of electric field is obtained, so that high therapeutic effects are exerted to the affected portion stably.

Figure 10:
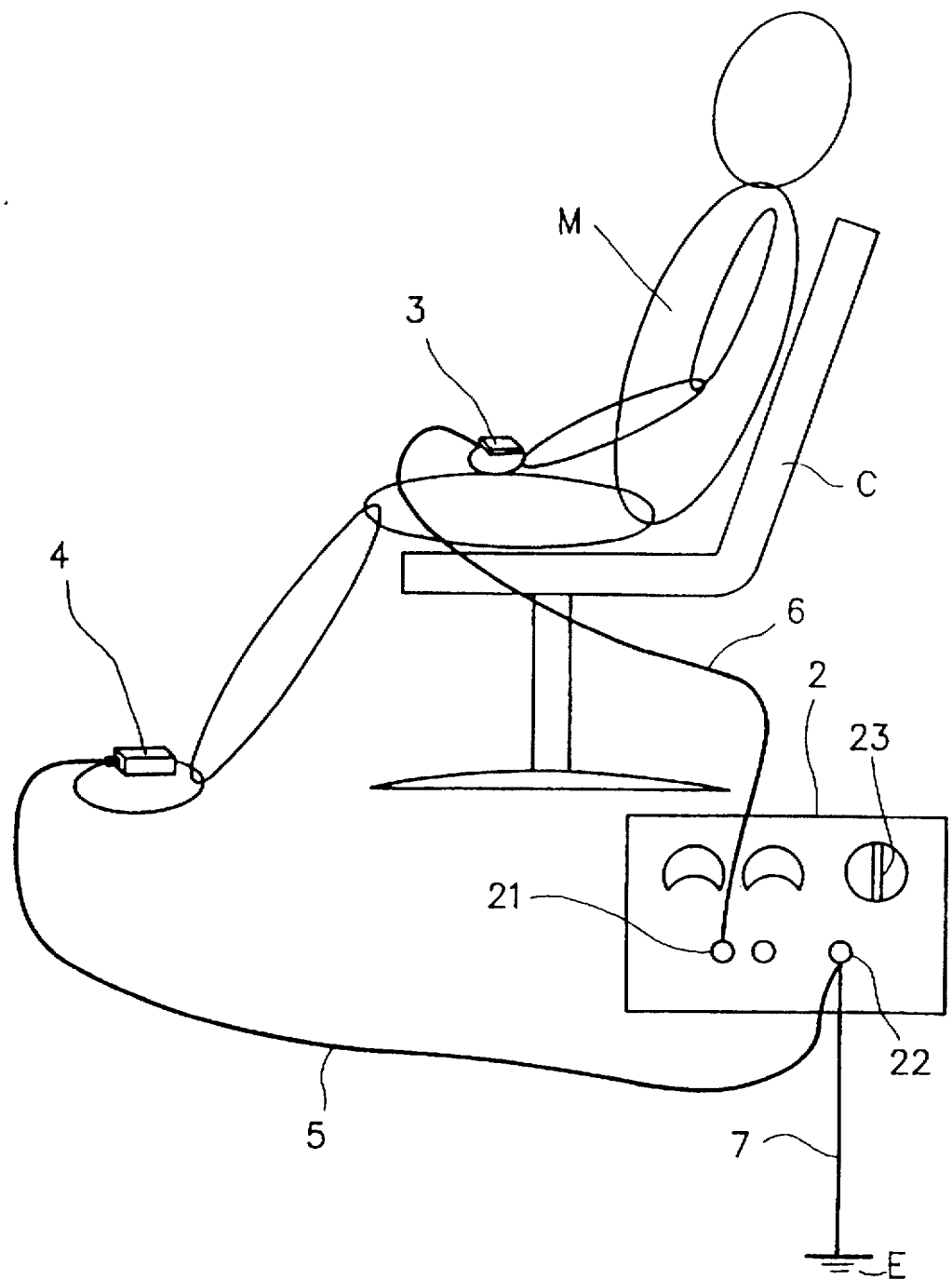
FIG. 10 is a view for explaining how to use the therapeutic apparatus utilizing electric potential for treating a patient.

In operation, as shown in FIG. 10, a patient M is sat on a chair C and the patient is insulated. Alternatively, the patient may be laid on a bed (not shown). The therapeutic plate 3 is contacted with a portion of the patient. On the other hand, the device 4 for increasing electric field is contacted with the affected portion to be treated. Under these conditions, negative electric potential is directly applied to the patient M from the output terminal 21 of the generator 2 of electric field through the therapeutic plate 3. As a result, a strong electric field (negative charge $e^-$) is applied to the affected portion to be treated and to the vicinity thereof, thereby carrying out therapy.

Experimental data will now be described. The therapeutic plate 3 was contacted with the back of one hand of the patient M and the device 4 for increasing electric field was contacted with the back of the other hand. The device 4 comprises a grounded conductor plate and the distance L between the surface of the conductor plate and the surface of the plastic case, which is contacted with the patient, was 5 cm. Negative direct voltage of 250V was applied to the patient from the output terminal 21 of the generator 2 of electric potential through the therapeutic plate 3, thereby applying negative charge ($e^-$) to the back of the hand. In this manner, three patients were treated. The results are as follows:

(A) In case of a female patient of 32 years old, she felt warm under the device for increasing electric field 60 seconds after the beginning of the application of voltage.

(B) In case of a female patient of 65 years old, she felt warm under the device for increasing electric field 90 seconds after the beginning of the application of voltage.

(C) In case of a male patient of 45 years old, he felt warm under the device for increasing electric field 120 seconds after the beginning of the application of voltage.

The negative charge ($e^-$) applied to the human body by applying the negative electric potential is circulated throughout the body together with body fluid. In the back of the hand on which the device 4 for increasing electric field is placed, since the earthed potential (grounded conductor plate 41) is located in a close position of about 5 cm, a capacitor is formed between the back of the hand and the grounded conductor plate 41, so that the negative charge ($e^-$) is concentrated to the back of the hand, that is, the electric field is concentrated to that portion, thereby topically warming the back of the hand.

The negative charge ($e^-$) applied to the human body is effective for relieving stiff shoulder, headache, low back pain, insomnia and chronic constipation, as well as for improvement of skin, poor circulation and other disorders.

We claim:

1. An electrical therapy apparatus for applying an electric field to a patient, said therapy apparatus comprising:

a power source connected to a ground terminal;

a first conductor, connected to and receiving power from said power source, said first conductor being directly applied to the patient during therapy;

an electric field device connected to the ground terminal and including a second conductor housed in an insulating case at a fixed distance from an application surface of the insulating case, the application surface of the insulating case being applied to the patient during therapy to generate an electric field.

2. The electrical therapy device according to claim 1, wherein the insulating case is hollow.

3. The electrical therapy device according to claim 1, wherein the insulating case is plastic.

4. The electrical therapy device according to claim 1, wherein the insulating case is solid except for a second conductor housing area.

5. The electrical therapy device according to claim 1, wherein the fixed distance between the second conductor and the application surface is 4 to 8 cm.

6. The electrical therapy device according to claim 1, wherein the second conductor is plate shaped with a handle which protrudes from one end of the insulating case.

7. The electrical therapy device according to claim 1, wherein the second conductor is not permanently fixed to the insulating case so that it may be removed from one end of the insulating case and later inserted therein.

8. The electrical therapy device according to claim 7, wherein the insulating case includes grooves for guiding the second conductor upon insertion into the insulating case.

9. The electrical therapy device according to claim 7, wherein the insulating case has a plurality of parallel slots, each slot a different distance from the application surface, the plurality of parallel slots allowing the second conductor to be set at different distances from the application surface.

10. The electrical therapy device according to claim 1, wherein said first conductor and said second conductor are the same conductor type.

11. An therapy method for applying an electric field to a patient, said therapy method using a device having a power source connected to a ground terminal, a first conductor receiving power from the power source, and a electric field device connected to the ground terminal, said therapy method comprising the steps of:

applying the first conductor directly to the patient;

applying the electric field device to the patient, the electric field device including a second conductor housed in an insulating case at a fixed distance from an application surface of the insulating case, the application surface of the insulating case being applied to the patient; and sending electrical power from the power source to said first conductor, thereby generating an electric field at the application surface of the insulating case applied to the patient.

12. The therapy method according to claim 11, wherein the insulating case is hollow.

13. The therapy method according to claim 11, wherein the insulating case is plastic.

14. The therapy method according to claim 11, wherein the insulating case is solid except for a second conductor housing area.

15. The therapy method according to claim 11, wherein the fixed distance between the second conductor and the application surface is 4 to 8 cm.

16. The therapy method according to claim 11, wherein the second conductor is plate shaped with a handle which protrudes from one end of the insulating case.

17. The therapy method according to claim 11, wherein the second conductor is not permanently fixed to the insulating case so that it may be removed from one end of the insulating case and inserted therein.

18. The therapy method according to claim 17, wherein the insulating case includes grooves for guiding the second conductor upon insertion into the insulating case.

19. The therapy method according to claim 17, wherein the insulating case has a plurality of parallel slots, each slot a different distance from the application surface, the plurality of parallel slots allowing the second conductor to be set at different distances from the application surface.

20. The therapy method according to claim 11, wherein the first conductor and the second conductor are the same conductor type.

* * * * *